US00PP18974P3

(12) United States Plant Patent
Stemkens

(10) Patent No.: US PP18,974 P3
(45) Date of Patent: Jun. 24, 2008

(54) *NEMESIA* PLANT NAMED 'NEMHMAGO'

(50) Latin Name: ***Nemesia* hybrid**
Varietal Denomination: Nemhmago

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 146 days.

(21) Appl. No.: 11/299,609

(22) Filed: Dec. 12, 2005

(65) Prior Publication Data

US 2007/0136908 P1 Jun. 14, 2007

(51) Int. Cl.
*A01H 5/00* (2006.01)

(52) U.S. Cl. ..... Plt./458

(58) Field of Classification Search ..... Plt./458, Plt./263

See application file for complete search history.

*Primary Examiner*—Anne Marie Grunberg
*Assistant Examiner*—Louanne Krawczewicz Myers
(74) *Attorney, Agent, or Firm*—S. Matthew Edwards

(57) ABSTRACT

A new and distinct variety of *Nemesia* plant, substantially as herein illustrated and described, characterized particularly as to novelty by a semi-trailing and compact habit, golden yellow flowers, very early flowering and absolutely no seed set.

1 Drawing Sheet

Latin name of the genus and species of the plant claimed: *Nemesia* hybrid.
Varietal denomination: 'Nemhmago'.

BACKGROUND OF THE NEW PLANT

The present invention relates to a new and distinct cultivar of *Nemesia* plant known botanically as *Nemesia* hybrid and that will be referred to hereinafter by the cultivar name 'Nemhmago.'

The new *Nemesia* is a product of a planned breeding program conducted by the inventor in Enkhuizen, The Netherlands. The goals of the breeding program were to improve on plant habit by breeding plants that were more compact and basal branching. Earliness of flowering was another character that was very important in the breeding process, together with producing no seed pods.

The new *Nemesia* originated from a cross-pollination made by the inventor in 2002 of an unpatented *Nemesia* plant, named 'D0366-2,' as the female, or seed, parent with an unpatented *Nemesia* plant named 'E0131-6,' as the male, or pollen, parent. The cultivar 'Nemhmago' was discovered and selected by the Inventor as a plant within the progeny from this cross-pollination in a controlled environment in Enkhuizen, The Netherlands, in 2003.

As a result of this cross the present cultivar was created in 2003 in Enkhuizen, Netherlands and has been repeatedly asexually reproduced by cuttings in Enkhuizen, Netherlands and Sarrians, France over a two year period. It has been found to retain its distinctive characteristics through successive propagations. The new variety is stable and reproduces true to type in successive generations of asexual reproduction.

DESCRIPTION OF THE DRAWING

This new *Nemesia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Nemesia*. The data which defines these characteristics were collected from asexual reproductions carried out in Enkhuizen, Netherlands. The plant history was taken on 14 week old plants, blossomed under natural light in a greenhouse, and grown in a 10.5 cm container.

Color readings were taken in the greenhouse under ambient light. Color references are primarily to The R.H.S. Colour Chart of The Royal Horticultural Society of London.

TABLE 1

DIFFERENCES BETWEEN THE NEW CULTIVAR 'NEMHMAGO,' ITS PARENTS AND A SIMILAR CULTIVAR

| | 'Nemhmago' | 'D0366-2' | 'E0131-6' | 'Sunsatia lemon' |
|---|---|---|---|---|
| Seed set | No | No | Plentiful | Few |
| Flower size | Very big | Medium | Very big | Medium |
| Flower color | Golden yellow | White | Orange | Light yellow |

The commercial name of the most resembling variety is 'Sunsatia lemon.' This variety is not known to be patented.

The plant:

*Classification.*—Botanical: *Nemesia* hybrid.

*Cultivar name.*—'Nemhmago'.

*Parentage.*—Female parent: A seedling named 'D0366-2' is one of our seedlings from our D-generation of plants bred in 2002. Pollen parent: A seedling named 'E0131-6' is one of our seedlings from our E-generation of plants bred in 2003.

*Growth habit.*—Semi-trailing and compact.

*Plant height.*—12–24 cm.

*Spreading area of plant.*—20–28 cm.

*Strength.*—Resistant to hot and cold weather.
*Branching character.*—Freely branching and lateral branching at every node.
*Number of branches per plant.*—35–65.
*Blooming period.*—From April until November.
*Propagation.*—Vegetative stem cuttings.
*Sexuality.*—Hermaphrodite.
*Time to initiate roots.*—Approximately 10 days at temperatures of 21 degrees centigrade is needed to produce cuttings.
*Root system.*—Numerous and fine, the color is N155A.

The stem:
*Diameter.*—3–4 mm.
*Length.*—12–14 cm.
*Shape.*—Quadrilateral with ridges.
*Anthocyan pigmentation.*—Absent.
*Color of the stem.*—137B.
*Length of internode.*—18–22 mm.
*Pubescence.*—Glabrous.
*Length lateral branches.*—10–12 cm.

The foliage:
*Phyllotaxis.*—Opposite.
*Shape of blade.*—Broadly ovate.
*Attachment.*—Petiolate.
*Texture.*—Upper side: Glabrous. Lower side: Glabrous.
*Venation.*—Pinnate.
*Leaf venation color.*—Upper surface: 133A. Lower surface: 137B.
*Leaf margin.*—Vegetative shoots: Entire. Generative shoots: Dentate.
*Leaf base.*—Obtuse to truncate.
*Leaf apex.*—Apiculate.
*Length.*—30–50 mm.
*Width.*—25–40 mm.
*Depth of incision.*—No incision.
*Color.*—Upper side: 135A. Lower side: 138A.
*Petiole length.*—1–2 mm.
*Petiole surface structure.*—Glabrous.
*Petiole diameter.*—2–3 mm.
*Petiole coloration.*'Upper side: 135A. Lower side: 135A.

The bud:
*Peduncle length.*—10–15 mm.
*Peduncle diameter.*—2–3 mm.
*Peduncle color.*—137B.
*Peduncle surface.*—Glabrous.
*Pedicel length.*—4–12 mm.
*Pedicel diameter.*—Less than 1 mm.
*Pedicel color.*—137C.
*Stipule length.*—1–2 mm.
*Stipule width.*—1–2 mm.
*Stipule shape.*—Lanceolate.
*Stipule color.*—Upper side: 137B. Lower side: 137B.
*Number of buds per plant at stage of observation.*—18–23 buds.
*Bud size.*—Diameter: 4 mm. Length: 3 mm.
*Bud shape.*—Globular.
*Bud color.*—N155B.
*Bud surface.*—Glabrous.
*Sepals.*—Color (Upper side): 137B. Color (Lower side): 137C. Form: Upright. Surface: Glabrous. Number: 5, fused. Length: 1–2 mm. Width: Less than 1 mm. Shape: Lanceolate. Apex: Apiculate. Base: Fused. Margin: Entire.

The flower:
*Type of inflorescence.*—Axillary raceme.
*Flower shape.*—Personate.
*Palate dimensions.*—2 mm in width and 1.5 mm in length.
*Palate color.*—Upper side: N25B. Lower side: Not visible.
*Nectary (located on the under side of palate).*—4 mm in width and 4 mm in length.
*Nectary color.*—149D.
*Throat color* (*upper surface*)—Inside color of the tube or throat.: 158B.
*Throat color* (*lower surface*)—Outside color of the corolla tube.: 157A.
*Corolla tube dimensions.*—5 mm in length and 1.5 mm in diameter.
*Corolla tube color.*—157A.
*Surface of upper lip.*—Upper side: Glabrous. Lower side: Glabrous.
*Surface of lower lip.*—Upper side: Glabrous. Lower side: Glabrous.
*Lip margin* (*lower lip*).—Entire.
*Lip margin* (*upper lip*).—Entire.
*Number of lips.*—2.
*Lobes.*—Upper lip: 4. Lower lip: 1.
*Lobes on upper lip fused or unfused.*—Fused.
*Lip apex* (*upper lip*).—Each lobe has a rounded apex.
*Lip base* (*upper lip*).—Fused.
*Lip apex* (*lower lip*).—Obtuse.
*Lip base* (*lower lip*).—Fused.
*Upper lip color.*—Upper side: 17A with venation 26A and an indentation (an eye) of N186B. Lower side: 18B with very irregular venation of 40B.
*Lower lip color.*—Upper side: 17A with venation of 26A. Lower side: 18B with very irregular venation of 40B.
*Indentation dimensions.*—3 mm in width and 1.5 mm in length.
*Indentation color.*—Upper side: N186B. Lower side: Not visible.
*Flower dimensions.*—1.1 cm in depth, 3 cm in length and 3.2 cm in width at the widest part.
*Lower lip dimensions.*—1.5 cm in length and 2.8 cm in width.
*Upper lip dimensions.*—1.4 cm in length and 3.2 cm in width.
*Lobe dimensions* (*upper lip*).—1.3 cm in length and 8 mm in width.
*Flower spur dimensions.*—2 mm in length and 1–2 mm in diameter.
*Spur color.*—22C.
*Calyx dimensions.*—4 mm in length and 5 mm in width.
*Calyx shape.*—Cup shaped, five pointed star.
*Calyx color.*—Upper side: 137B. Lower Side: 137C.
*No. of flowers per inflorescence.*—35–60.
*Fragrance.*—No fragrance.
*Bloom time of one inflorescence.*—New florets continue to open in one inflorescence over a period of 32 days.
*Lastingness of a single flower on the plant.*—3–7 days.
*Lastingness of a single flower off the plant.*—Less than 6 hours.

The reproductive organs:
*Androecium.*—Stamens quantity: 4. Anther shape: ovoid. Anther length: 0.3 mm. Anther width: 0.2 mm. Anther color: 154D. Pollen amount: No pollen.
*Gynoecium.*—Pistils quantity: 1. Pistil length: 3–5 mm. Stigma color: 144C. Style length: 3–5 mm. Style color: 144D. Ovary color: 144C. Ovary position: Superior. Ovary shape: Oval. Ovary dimensions: 0.3 mm in width and 0.4 mm in length.

Seeds: No seed set is observed. No fruits are formed.

Disease and pest susceptibility or resistance: There are no disease problems known to the inventor other than what effects typical *Nemesia*.

What is claimed is:

1. A new and distinct cultivar of *Nemesia* plant named 'Nemhmago,' as substantially illustrated and described herein.

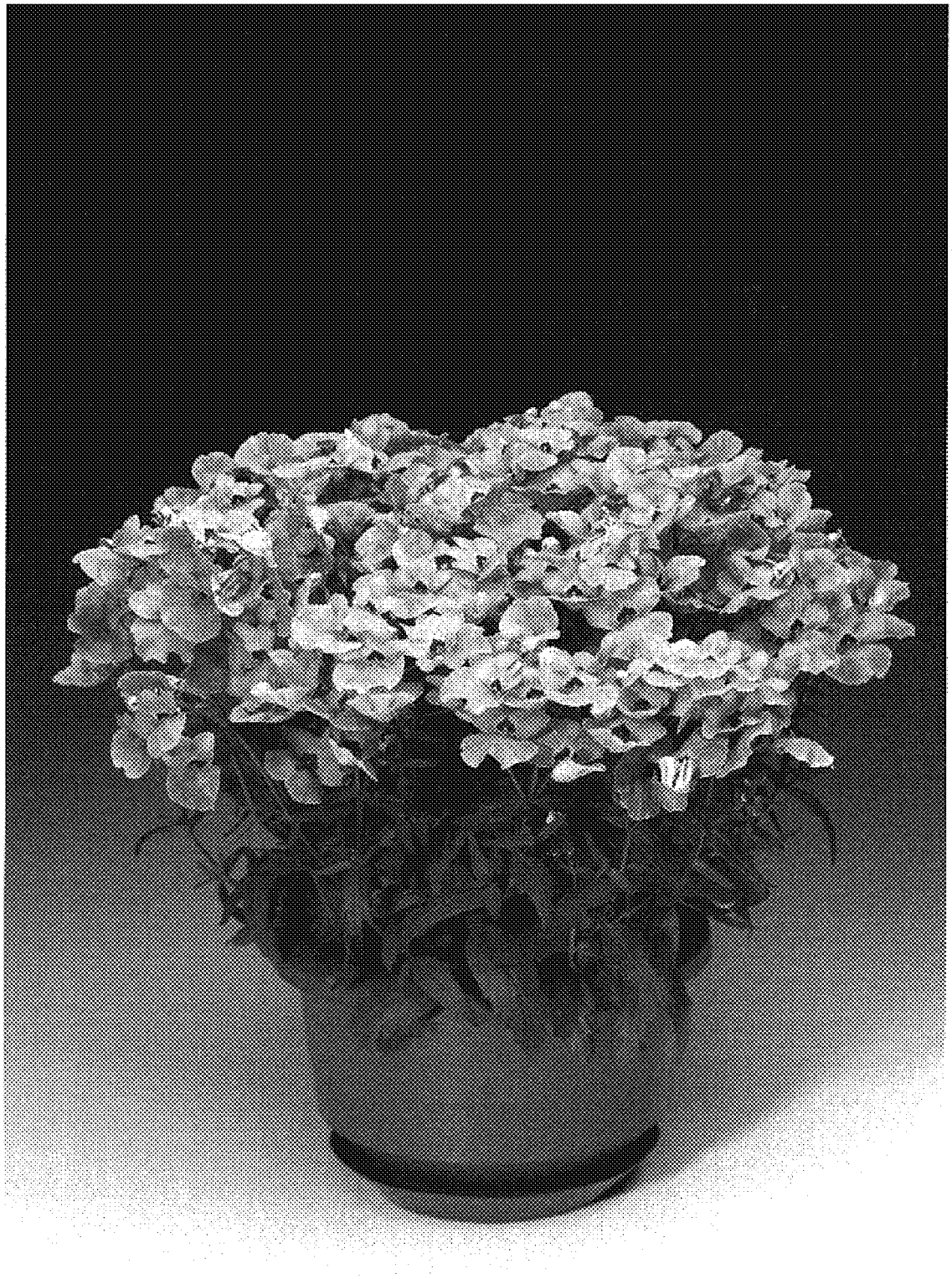

* * * * *